(12) United States Patent
Cummings et al.

(10) Patent No.: US 8,776,610 B2
(45) Date of Patent: Jul. 15, 2014

(54) APPARATUS FOR MEASURING FAILURE LOAD OF MODEL TRUSS STRUCTURES

(71) Applicants: Brent Cummings, Walla Walla, WA (US); Dallas Jones, Walla Walla, WA (US)

(72) Inventors: Brent Cummings, Walla Walla, WA (US); Dallas Jones, Walla Walla, WA (US)

(73) Assignee: Fluid Learning Uniquely Executed, LLC, Walla Walla, WA (US)

( * ) Notice: Subject to any disclaimer, the term of this patent is extended or adjusted under 35 U.S.C. 154(b) by 126 days.

(21) Appl. No.: 13/648,315

(22) Filed: Oct. 10, 2012

(65) Prior Publication Data

US 2014/0096617 A1 Apr. 10, 2014

(51) Int. Cl.
*G01L 19/00* (2006.01)
*G01N 19/00* (2006.01)

(52) U.S. Cl.
USPC .............................................. 73/804; 73/818

(58) Field of Classification Search
USPC .................... 73/760, 788, 796, 804, 818, 856
See application file for complete search history.

(56) References Cited

U.S. PATENT DOCUMENTS

| | | | |
|---|---|---|---|
| 2,446,566 A | 8/1948 | Wenk | |
| 5,178,017 A | 1/1993 | Dinzburg | |
| 5,195,378 A * | 3/1993 | Ferguson | 73/790 |
| D351,804 S | 10/1994 | Kellstedt et al. | |
| 5,413,306 A | 5/1995 | Mahoney | |
| 6,332,364 B1 * | 12/2001 | Buschmann et al. | 73/788 |
| 6,418,776 B1 * | 7/2002 | Gitis et al. | 73/10 |
| 7,178,406 B2 * | 2/2007 | Gonzalez et al. | 73/856 |
| 7,284,447 B2 * | 10/2007 | Scarborough | 73/850 |
| 7,938,015 B2 | 5/2011 | Kaneda | |
| 2006/0003877 A1 * | 1/2006 | Harmon | 482/142 |
| 2006/0191352 A1 | 8/2006 | Lewellen | |

* cited by examiner

*Primary Examiner* — Max Noori
(74) *Attorney, Agent, or Firm* — Adler Vermillion, LLP (57) ABSTRACT

An educational force application and force measurement apparatus is with a plurality of interchangeable workpiece mounting components is disclosed. The apparatus securely accepts a model structure (workpiece), secures a force measurement component between the model structure and a force application component, and applies an incrementally increasing force until the workpiece fails. A series of interchangeable upper workpiece mounting components allow the apparatus to measure the failure load on several different types of model structures.

19 Claims, 5 Drawing Sheets

APPARATUS FOR MEASURING FAILURE LOAD OF MODEL TRUSS STRUCTURES

CROSS REFERENCES TO RELATED APPLICATIONS

None.

FIELD OF INVENTION

The technology relates to the general field of measuring failure loads in truss structures, and has certain specific application to measuring the failure loads of student designed model structures, of varying shapes and sizes, in a demonstrative and engaging manner, as part of an educational curriculum.

BACKGROUND

The technology relates to the field of measuring failure loads on truss structures. In particular, it relates to exerting an incrementally increasing load on a model structure, and measuring the failure load in a demonstrative and engaging manner as part of an educational curriculum.

In teaching a science or engineering curriculum, it is important to allow students to experiment with their own designs. Environments that allow for exploration, interaction and engagement tend to encourage learning. Such an environment stimulates intellectual curiosity and helps young learners develop into independent learners. However, the classic "chalk-and-talk" style lectures generally fail to encourage this type of experimental learning. Instead, the curriculum is narrowly confined, creativity is stifled, and learning is hindered. The disclosed technology provides a useful tool for creating an atmosphere of continuous give-and-take between students and educators, and an adaptive learning environment.

In an initial trial, students are given materials and broad objectives, but all content-based information is withheld. Rather than build from a template, students are encouraged think creatively. Students will make a series of predictable mistakes, but they will learn more from their own design mistakes than from a traditional lecture.

But traditional truss measurement devices are unsuitable for this type of creative experimentation. They fail to adapt to the different truss styles and sizes that students create. Through careful research in the field of engineering education, the inventors have identified the most common student design errors. The disclosed apparatus was developed to adaptably accept all of the most common student designs.

For example, many students build bridges with square trusses. These square trusses tend to lean and give on a sideways break. The disclosed technology provides an apparatus that anticipates these design errors, and measures the failure load in an engaging and educational fashion. When measuring failure loads, the disclosed design keeps the student structure (the workpiece) readily visible to the entire class.

Furthermore, where a measurement device is too complicated, students fail to engage in the curriculum. The disclosed apparatus is designed to provide a simplified, collapsible, affordable, and stylish educational tool.

SUMMARY

The disclosed apparatus applies a force on a workpiece, measures the force, incrementally increases the force, and repeats the process until the applied force reaches the truss' failure load, and the truss collapses. The work-piece (the structure being tested) may be a model bridge, truss, tower or crane or similar structure.

The robust design and interchangeable components allow for rapid assembly. The apparatus may be used by educators as part of a curriculum in science, engineering or structural design. The clean industrial appearance attracts students and helps keep them engaged.

Use. The workpiece is placed in the upper component and secured in place. A harness is connected to the truss. At the other end of the harness, it is connected to a hanging scale. A vice-jack is cranked to apply force to the workpiece through the scale, cable and breaking feature.

Flexible Design: The Apparatus is designed to accept a variety of different structures as the workpiece. A series of holes along the upper horizontal crossbrace allow for variability of function within and between curriculums. Additionally, a plurality of holes spaced along on the vertical posts allow for additional flexibility between curriculums.

DETAILED DESCRIPTION

The following is a detailed description of exemplary embodiments. The embodiments are provided to illustrate aspects of the invention and should not be construed as limiting the scope of the invention.

Figure 1:
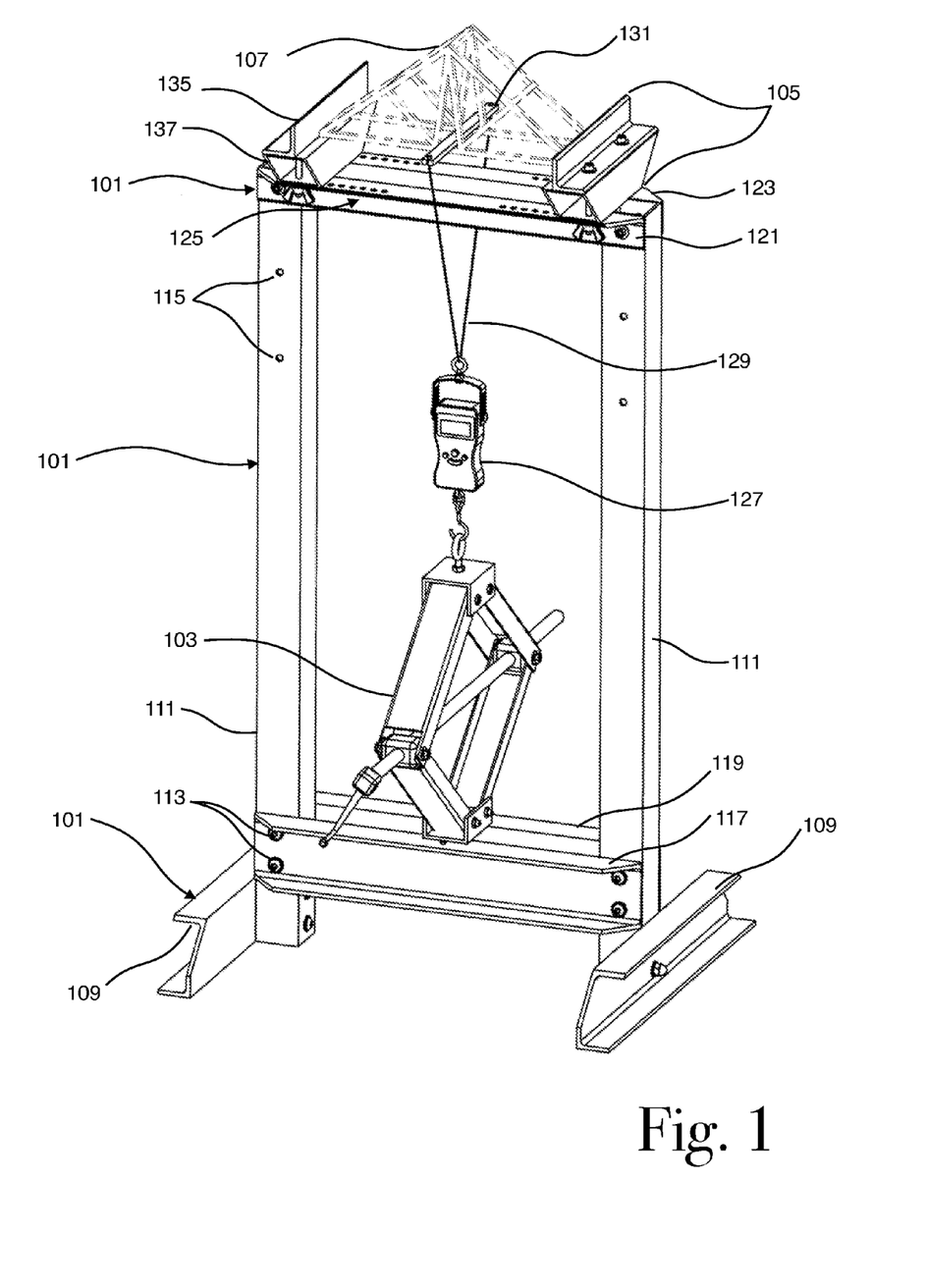
FIG. 1 illustrates a three-quarter view of an embodiment with a truss-type top component and a workpiece drawn in dashed lines.

FIG. 1—Overview. FIG. 1 illustrates a three-quarter view of an embodiment of the apparatus.

Support Structure. The support structure 101 is a series of beams and posts. The support structure holds the force application component 103 in place. It also holds one of a plurality of interchangeable upper components 105 in place. The upper component 105, in turn, is securely attachable to a workpiece 107.

In one embodiment, the support structure 101 is made of aluminum beams secured together with bolts and wingnuts. This allows the apparatus to be easily assembled for use, and disassembled for storage and transportation.

Stabilizing Brackets. In this embodiment, two horizontal stabilizing brackets 109 run parallel to each other, and are spaced apart from each other. These brackets 109 keep the support structure 101 standing upright during use. Horizontal stabilizing brackets 109 may be square channel beams (C-Beams) made of aluminum. This tends to promote ease of assembly while maintaining a favorable strength-to-weight ratio.

In other embodiments, the horizontal stabilizing brackets may run at non-parallel angles. In other embodiments, the support structure 101 may be bolted directly to a table, or otherwise secured to an immovable object in a manner that allows for a plurality of people to view the apparatus.

Vertical Posts. A vertical post 111 is secured to each horizontal stabilizing bracket 109. In the present embodiment, two bolts 113 are used to secure each vertical post 111 to its corresponding stabilizing bracket 109. These vertical posts 111 are at least tall enough to hold a workpiece 107 over a force-application device 103 and force-measuring device 127. Each vertical post 111 is adapted to securely accept a face of an Upper Horizontal Crossbrace 121, 123.

In the present embodiment, the vertical posts 111 are square hollow-structural-section beams, and include a series of vertically spaced sockets 115 along their body. The vertically spaced sockets 115 are adapted to accept various interchangeable upper components 121, 123 at different heights.

Lower Horizontal Crossbrace. A lower horizontal crossbrace 117 is secured to a side of each of the Vertical Posts 111. These horizontal crossbraces run orthogonally to both the stabilizing brackets 109 and the vertical posts 111. In a preferred embodiment, there are two lower horizontal crossbraces 117, 119 each secured to an opposite side of both Vertical Posts 111 by bolts 113. Each bolt may run through a first lower horizontal crossbrace 117, a vertical post 111, and a second lower horizontal crossbrace 119.

Upper Horizontal Crossbrace. An Upper Horizontal Crossbrace 121 is secured to a first vertical post 111 and a second vertical post 111. In a preferred embodiment, a second Upper Horizontal Crossbrace 123 is also secured to a first vertical post 111 and a second vertical post 111.

An Upper Horizontal Crossbrace 121 includes a plurality of sockets 125 along its length, each socket capable of accepting a bolt. These sockets allow an Upper Horizontal Crossbrace 121 to mate with one of a plurality of interchangeable upper components (displayed in the present embodiment is the Truss-Type component 105).

In a preferred embodiment, the Upper Horizontal Crossbrace 121 has an "L-shaped" cross-section.

Materials. In one embodiment, the Posts 111 and Crossbraces 117, 119, 121, 123 are made from aluminum with a brushed finish. The bolts and wingnuts may be made from black zinc.

Force Application Component. A force application component 103 is secured to a lower horizontal crossbrace 117. In one embodiment, the force application component 103 is a standard hand-operated jack. The force application component 103 may be bolted to an upper face of the lower horizontal crossbrace 117.

In a preferred embodiment, the force application component 103 is a Torin brand 1-ton scissor jack, Model # T10102, with a lift height of between 3.5 inches and 15 ¹⁄₁₆ inches.

Force Measurement Component. An end of a Force Measurement Component 127 is secured to an upper portion of the force application component 103. In one embodiment, the force application component is a digital hanging scale. In another embodiment, the Force Measurement Component 127 is an American Weigh brand 110 lb×1 oz digital hanging scale (model no. H-110).

An end of a cable 129 is secured to an upper end of the Force Measurement Component 127. The cable is, in turn, secured to a one of several interchangeable Harness mechanisms.

Interchangeable Harness. The harness is attachable to the workpiece 107 in a manner that allows the apparatus to apply a predictable and repeatable force to the workpiece. The apparatus includes a plurality of interchangeable harness options to securely attach to different types of workpiece structures. These harness options include, for example, a bridge or truss-type harness 131, and a tower breaking plate harness.

In a preferred embodiment, the Truss-Type Harness includes a beam 131 and a cable 129. One end of a cable 129 is secured to one end of the beam 131, the wire runs through the force measurement device 127 (e.g. a hanging scale), and a second end of the wire is removably-secured to a second end of the beam 131. The wire 127 may be, for example, a 1.2 mm diameter cable.

In an exemplary embodiment, the cable is a 1×19 stainless steel "inner wire." An "inner wire" being the type of wire commonly found in motorcycle or bicycle cable-pull brakes or shifters. 1×19 refers to the final wire being made of 19 wires wound together to make a single wire. A 1.2 mm stainless steel 1×19 inner wire results in a strong, thin, flexible wire that looks attractive to students.

The exemplary cable terminates at each end with ball-end fittings. In an exemplary embodiment, the harness includes three interchangeable cables, on each of 19 inches, 23 inches and 30 inches in length. Different length cables may be used in conjunction with towers of different heights, and also help the apparatus adapt to accept "deck truss" type model truss structures (that is, model bridges designed with a "deck" above the trusses rather than below the trusses).

Other embodiments may include, for example, a 1.5 mm 7×7 stainless steel inner wire (that is, seven of the 7×1 type wires wound together to make a final wire).

The tower-type Harness (see FIG. 4) includes a tower-breaking plate 413 and a cable 415. The tower-breaking plate 413 is adapted to securely engage the upper face of a tower-type workpiece 409. In one embodiment, the tower-breaking 413 plate is 0.25 inches tall by 5 inches wide by 5 inches long. The tower-breaking plate 413 also includes a hole 419 drilled through the center, adapted to accept a ball-end wire fitting 417.

Figure 4:
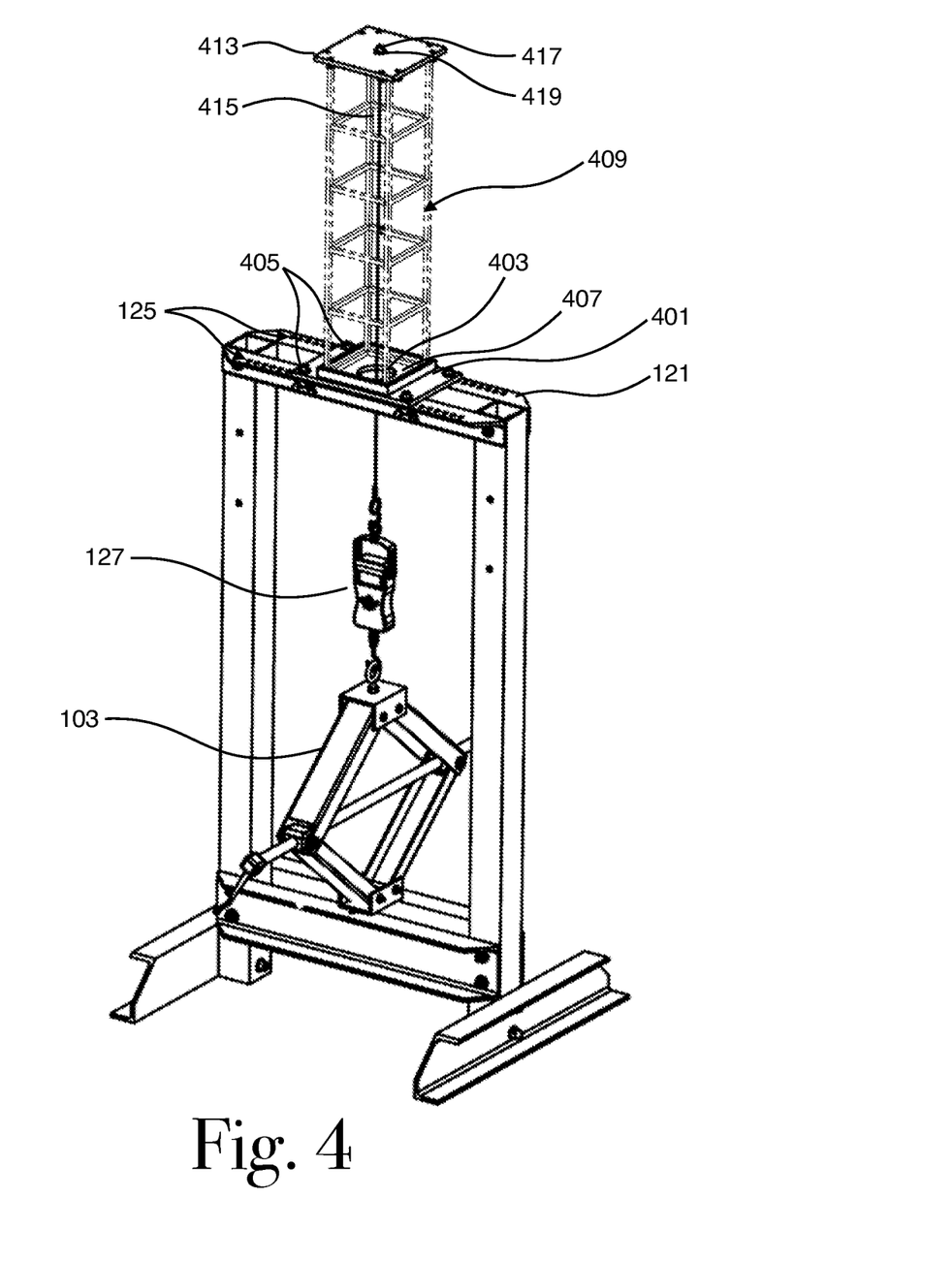
FIG. 4 illustrates a three-quarter view of an embodiment with a tower-type top component and a workpiece drawn in dashed lines.

The harness includes a cable, which terminates at each end with ball-end fittings. One of the ball-end fittings secures to the tower-breaking plate, the cable then travels through the tower base plate 410, and secures to the Force Measurement Component 127.

In another embodiment, the tower-type harness is a notched "breaking strap cross." The breaking strap cross is made of two beams, with corresponding notches in the center of the beam, wherein the notches allow the two beams to mate in an "X" shape. In a preferred embodiment, the beams are aluminum beams measuring approximately 0.25 inches tall by 0.4 inches wide by 8 inches long. The beams also include a hole drilled through the center, adapted to accept a ball-end wire fitting. The wire includes such a ball-end, which secures to the tower breaking plate, travels through the tower base plate, and secures to the force measurement component 127.

Dimensions. In the present embodiment, the total height of the assembled apparatus is 39.5 inches, and the total width is 21 inches. In other embodiments, the dimensions may be as small as 20 inches by 9 inches, and as large as 60 inches by 120 inches. In another embodiment, the Stabilizing Brackets 109 are 18 inches long. In other embodiments, the Stabilizing Bracket 109 length is adjusted as necessary to prevent the Apparatus from tipping over during operation.

Flexible Design: The Apparatus is designed for maximum interchangeability on the top. A series of sockets 125 along the upper horizontal crossbrace allow for variability of function within and between curriculums. In a preferred embodiment, the sockets are spaced ½' apart from each other.

Side View.

Figure 2:
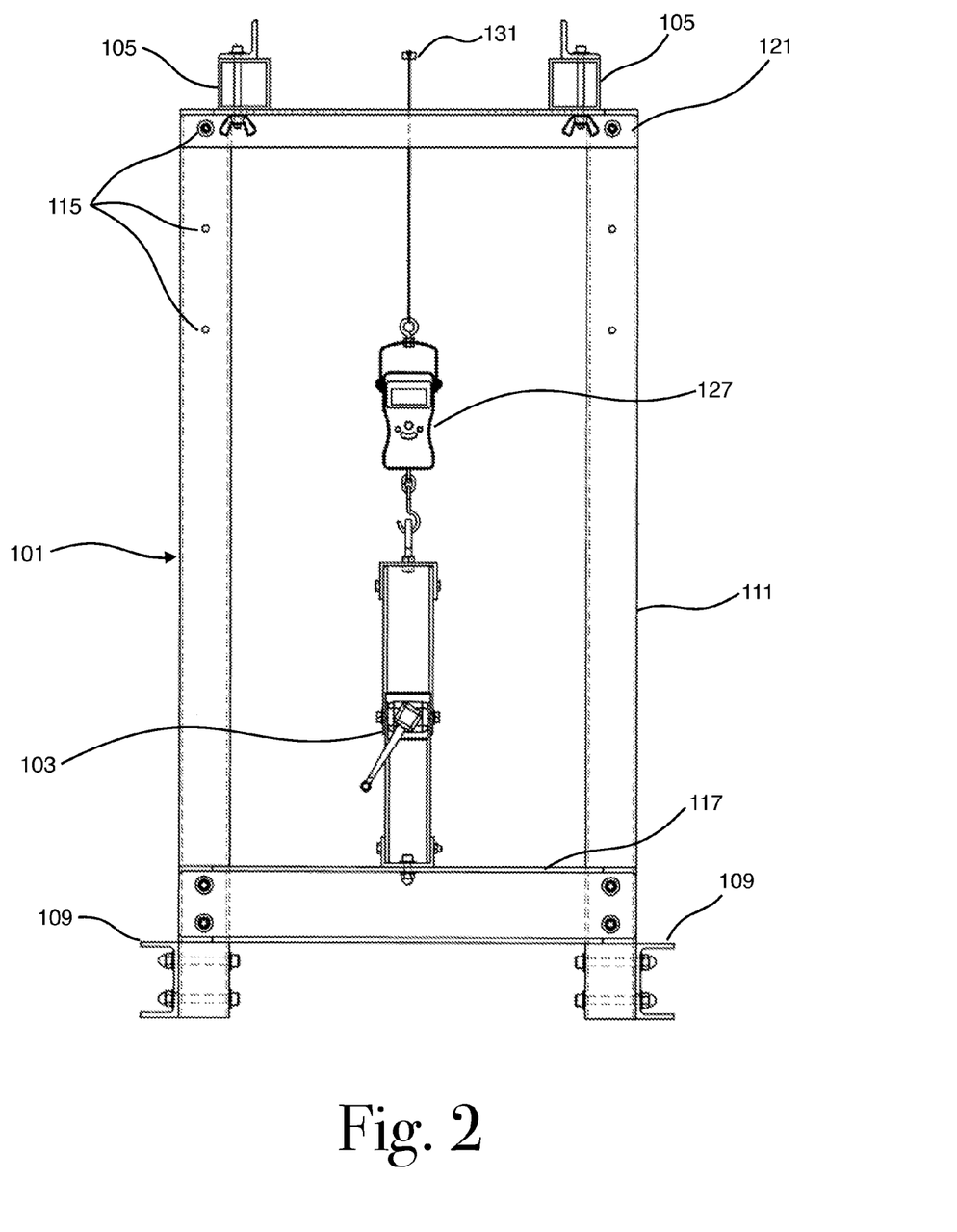
FIG. 2 illustrates a side-view of an embodiment with a truss-type top component.

FIG. 2. FIG. 2 depicts a side view of a preferred embodiment. Horizontal stabilizing brackets 109 are secured to vertical posts 111. A first end of a lower horizontal crossbrace 117 is secured to a first end of a first vertical post 111. A second end of a lower horizontal crossbrace 117 is secured to a first end of a second vertical post 111. At another end of the Vertical Posts 111, they are secured to respective ends of an Upper Horizontal Crossbrace 121. An interchangeable upper component 105 is secured to an upper face of the upper horizontal crossbrace 121.

A lower end of a force application component 103 is secured to an upper face of the lower horizontal crossbrace 117. An upper end of the force application component 103 is secured to a force measurement component 127. A harness 131 is secured to an upper end of the force measurement component 127. This harness is securable to a model bridge or truss-type workpiece (not shown in FIG. 2).

A plurality of sockets 115 in the vertical posts 111 allow the upper horizontal crossbrace 121 to be set at a several different heights, allowing the user to create different configurations and different model testing environments.

Top View.

Figure 3:
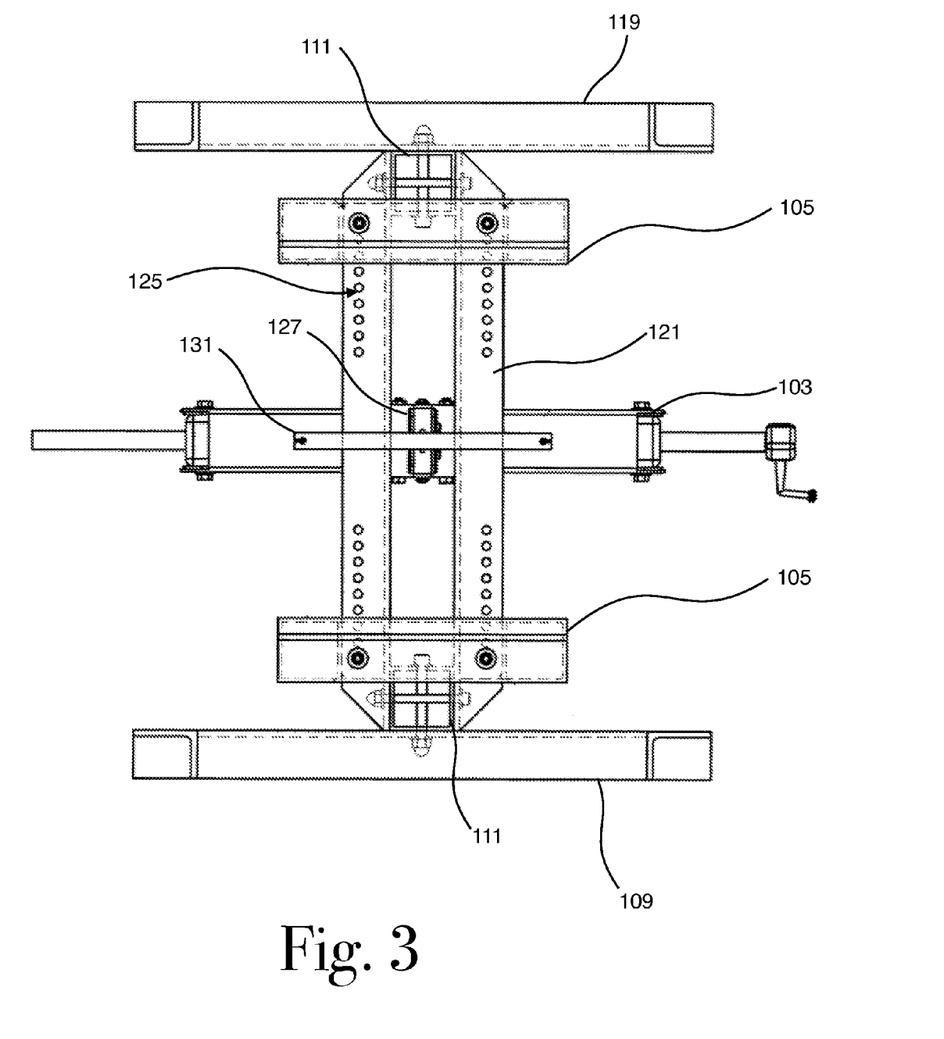
FIG. 3 illustrates a top-view of an embodiment with a truss-type top component.

FIG. 3 depicts a top-view of an embodiment with a model bridge or truss-type upper component.

Horizontal stabilizing brackets 109 are secured to vertical posts 111. A lower horizontal crossbrace (hidden in FIG. 3) is secured to the vertical posts 111. At a second end of the vertical posts, they are secured to respective ends of an upper horizontal crossbrace 121. An interchangeable upper component 105 is secured to an upper face of the upper horizontal crossbrace 121.

In this embodiment, the vertical posts 111 have a square cross section. This allows various components to be quickly secured to the vertical posts 111 with bolts and wingnuts.

A plurality of sockets 125 are spaced along the upper horizontal crossbrace 121. These sockets accept bolts, and allow interchangeable upper components to be secured to the upper horizontal crossbrace 121 at a plurality of different positions, which allows the user to create a variety of different testing environments.

A lower end of a force application component 103 is secured to an upper face of the lower horizontal crossbrace (not shown in FIG. 3). An upper end of the force application component is secured to a force measurement component. A harness 131 is secured to an upper end of the Force measurement component. This harness 131 is securable to a model bridge or truss-type workpiece (not shown in FIG. 3).

Interchangeable Upper Component. The upper component is securable to a workpiece. A plurality of interchangeable upper components are available. Different upper components are designed to secure different types of workpiece.

In an exemplary embodiment, the workpiece is a model bridge, and top-component is an abutment.

Upper Component: Bridge/Truss.

To test truss or model bridge structures, the bridge abutment upper component 105 is secured to the apparatus. The bridge abutment upper-component consists of a first and second abutment 105. In a preferred embodiment, the abutments include a length of aluminum bent at 90 degrees 135. The abutments are secured to angle support tubes 137, which are in turn secured to the upper horizontal crossbrace 121. The abutments and angle support tubes are secured to the to the upper horizontal crossbrace by a bolt and wingnuts assembly, secured at opposite ends of the crossbrace, and secured at approximately right angles with respect to the crossbrace.

A model bridge or truss may then be placed upon the abutments, with a first end of the bridge resting on the first abutment, and a second end of the bridge resting on a second abutment.

The harness 131 is then secured to the workpiece 107 through the approximate center of the workpiece. The harness wire 129 is secured to the force measurement mechanism 127, which is in turn secured to the force application mechanism 103.

As in the other configurations, the force application mechanism 103 is then used to apply an incrementally increasing force to the workpiece. After each incremental increase, a reading is taken from the force measurement component 127. The increment and measure process is repeated until the applied load is equivalent to the failure load and the tower collapses buckles or otherwise fails.

Upper Component: Tower.

FIG. 4 depicts a three quarter view of an embodiment with an upper component adapted to accept a model tower-type workpiece. In the tower configuration, a tower-baseplate 401 is secured to the upper component 121. The tower-baseplate 401 is a flat rectangular sheet. In an exemplary embodiment, it is made of aluminum. The tower-base-plate 401 includes a center-hole 403 with a radius of about 2 inches. This center-hole allows the force-applying wire to run through the tower-baseplate. The tower-baseplate also includes holes with recessed sockets 405 that are sized and spaced to accept bolts, and that align the bolts with corresponding sockets 125 in the upper component 121. In an exemplary embodiment, the tower-baseplate 403 includes an upper layer of rubber matting 407.

To use the apparatus in the tower configuration, a model tower 409 is placed atop the tower-baseplate 401, standing vertically. A tower-type Harness 413 is placed atop the workpiece.

A wire 415 with a ball-end 417 is strung through the ball-end fitting 419 at the center of the tower-type Harness 413. The wire 415 runs through the tower-workpiece 409 and the Tower Base-Plate 401. The opposite end of the wire is attached to the force-measurement 127 device, which is in turn attached to the force-application device 103.

As in the other configurations, force is then incrementally applied and measured. The increment and measure process is repeated until the applied load is equivalent to the failure load and the tower collapses buckles or otherwise fails.

Crane-Type Upper Component.

Figure 5:
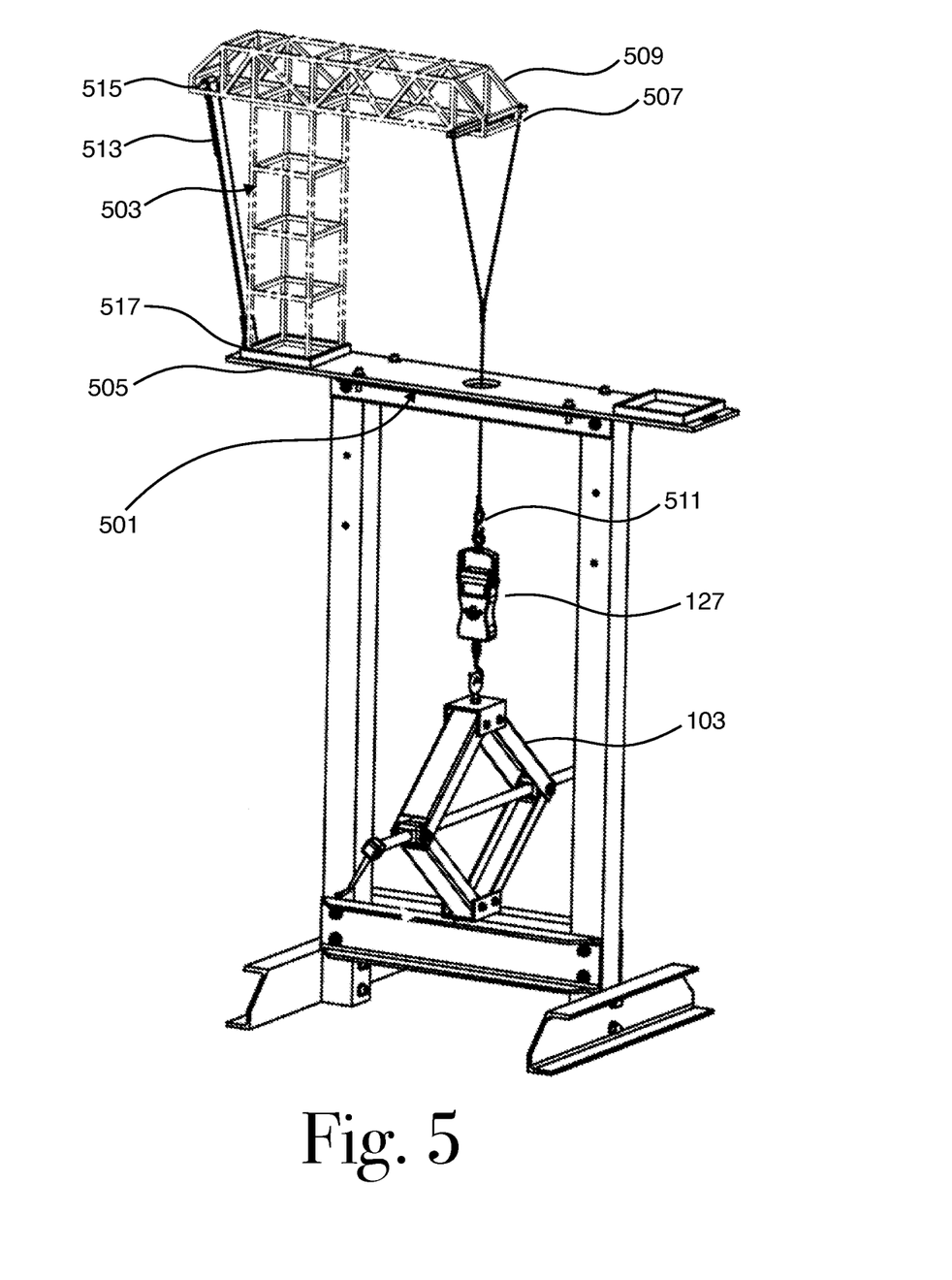
FIG. 5 illustrates a three-quarter view of an embodiment with a crane-type top component and a workpiece drawn in dashed lines.

FIG. 5 illustrates the apparatus with a crane-type upper component 501. The crane configuration accepts an asymmetric structure 503 (for example, a model crane).

A crane platform 505 is secured to one end of the crane-type upper component 501. The crane platform 505 includes sockets adapted to align with sockets in the upper component 501 in a manner that allows the Crane Platform to be securely bolted to the upper component.

In an exemplary embodiment, an "anchor strap" 513 acts like a counterweight on the model crane structure. One end of the anchor strap 513 is attached to an upper surface of the crane-type upper component at 517. A second end of the anchor strap is attached to a model crane structure at 515. The anchor strap 513 may be made from a Velcro strap for easy adjustment between model cranes of various sizes.

In an another embodiment, the crane-type upper component includes a vise or clamp on its upper surface. The vise is adapted to securely grasp the base of a model structure.

To use the apparatus in the crane configuration, the base of the model crane 503 is secured to the upper face of the Crane Platform 505. An end of a wire 507 is secured to the end of the crane arm 509. A second end of the wire 511 is attached to the force measurement device 127, which is in turn attached to the force application device 103.

As in the other configurations, force is incrementally applied and measured. The increment and measure process is repeated until the applied load is equivalent to the failure load and the crane workpiece collapses, buckles or otherwise fails.

Conclusion. The disclosed embodiments are illustrative, not restrictive. While specific configurations of the technology have been described, it is understood that the present invention can be applied to a wide variety of technology category. There are many alternative ways of implementing the invention.

What is claimed is:

1. A force application and measurement apparatus adapted to interchangeably engage a plurality of upper components, comprising,
   a. a support structure with an upper face and a lower horizontal crossbrace, a force application component, a force measurement component, and a harness, wherein,
   b. the upper face of the support structure includes a plurality of sockets,
   c. a first end of the force application component is secured to an upper face of the lower crossbrace,
   d. a second end of the force application component is secured to a first end of the force measurement component,
   e. a second end of the force measurement component is secured to a first end of the harness, and
   f. a second end of the harness is securable to a workpiece.

2. The force application and measurement apparatus of claim 1, further comprising an abutment upper component, where
   a. the abutment upper component includes a first abutment and a second abutment, and where,
   b. the first abutment is removably securable to the upper face of the support structure at one of a plurality of selectable locations, and
   c. the second abutment is removably securable to the upper face of the support structure at a plurality of selectable locations, and
   d. when so secured, the abutment components are adapted to securely receive a bridge-type or truss-type workpiece.

3. The force application and measurement apparatus of claim 1, further comprising, a tower-type upper component, wherein,
   a. the tower component is securable to the upper face of the support structure at a plurality of selectable locations,
   b. wherein the harness is a tower-type harness comprising a tower-plate and wire, wherein the tower-plate is perforated by a hole adapted to accept a ball-end wire fitting, and the wire terminates at one end with such a ball-end fitting thereby securing the wire to the tower plate, and
   c. the tower harness is securable at the tower-plate end to a top face of a tower-type workpiece, and securable at another end to the force measurement apparatus.

4. The force application and measurement apparatus of claim 1, further comprising, a crane upper component,
   a. the crane component includes a crane platform, an anchor strap, and a truss-type harness, wherein,
   b. the tower platform is securable to the upper face of the support structure at a plurality of selectable sockets,
   c. the anchor strap is secured, at one end, to an upper face of the tower platform, and is securable at a second end to a workpiece,
   d. the tower harness is securable at one end to a crane-type workpiece, and securable at a second end to a force measurement apparatus.

5. The force application and measurement apparatus of claim 1, further comprising, an abutment upper component and a crane upper component.

6. The force application and measurement apparatus of claim 1, further comprising, a tower upper component and a crane upper component.

7. The force application and measurement apparatus of claim 1, further comprising, an abutment upper component and a tower upper component.

8. The force application and measurement apparatus of claim 1, further comprising, an abutment upper component, a tower upper component and a crane upper component.

9. The force application and measurement apparatus of claim 1 wherein the support structure is made of aluminum beams secured to each other by a plurality of bold-and-wing-nut assemblies.

10. The force application and measurement apparatus of claim 1 where the height of the assembled support structure is between 20 inches and 60 inches, and the width of the assembled support structure is between 10 inches and 40 inches.

11. The force application and measurement apparatus of claim 1 where the height of the assembled support structure is approximately 40 inches, and where the width of the assembled support structure is approximately 20 inches.

12. The force application and measurement apparatus of claim 1 where the Force application device is a scissor jack and the Force measurement device is a hanging scale.

13. The force application and measurement apparatus of claim 1 where the harness cable is a 1×19 stainless steel inner wire.

14. The force application and measurement apparatus of claim 1, where the support structure's vertical elements include a plurality of sockets along their length, and wherein the sockets are adapted to receive the upper component at a plurality of different heights.

15. A force application and measurement apparatus adapted to interchangeably engage a plurality upper components, comprising,
   a. a plurality of horizontal stabilizing brackets, a plurality of vertical posts, a lower horizontal crossbrace, an upper horizontal crossbrace, a force application component, a force measurement component, and a harness, wherein,
   b. the horizontal stabilizing brackets are secured to a first end of the vertical posts,
   c. a first end of the lower horizontal crossbrace is secured to a first face of a first vertical post, and a second end of the lower horizontal crossbrace is secured to a first face of a second vertical post,
   d. a first end of the upper horizontal crossbrace is secured to a second end of a first vertical post, and a second end of the upper horizontal crossbrace is secured to a second end of a second vertical post,
   e. a face of the upper horizontal crossbrace includes a plurality of sockets,
   f. a first end of the force application component is secured to a face of the lower horizontal crossbrace,
   g. a second end of the force application component is secured to a first end of the force measurement component,
   h. a second end of the force measurement component is secured to a first end of the harness, and
   i. a second end of the harness is securable to a workpiece.

16. The force application and measurement apparatus of claim 2, further comprising an abutment upper component, wherein a. the abutment upper component includes, a first abutment and a second abutment, wherein,
b. the first abutment is removably securable to the upper horizontal crossbrace at a one of a plurality of available sockets, and
c. the second abutment is removably securable to the upper horizontal crossbrace at a one of a plurality of available sockets, and
d. when so secured, the abutment components are adapted to securely receive a bridge-type or truss-type workpiece.

17. The force application and measurement apparatus of claim 2, further comprising, a tower-type upper component, wherein,
a. the tower component includes a tower platform perforated by series of sockets alignable to sockets on the upper horizontal crossbrace, allowing the tower platform to be securely bolted to the upper horizontal crossbrace at a plurality of locations,
b. wherein the harness is a tower-type harness comprising a tower-plate and wire, wherein the tower-plate is perforated by a hole adapted to accept a ball-end wire fitting, and the wire terminates at one end with such a ball-end fitting thereby securing the wire to the tower plate, and
c. the tower harness is securable at the tower-plate end to a top face of a tower-type workpiece, and securable at another end to the force measurement apparatus.

18. The force application and measurement apparatus of claim 2, further comprising, a crane upper component,
a. the crane component includes a crane platform, an anchor strap, and a harness, wherein,
b. the crane platform is perforated by series of sockets alignable to sockets on the upper horizontal crossbrace, allowing the crane platform to be securely bolted to the upper horizontal crossbrace,
c. the anchor strap is secured, at a first end, to an upper face of the crane platform, and is securable at a second end to a workpiece, and
d. the harness is securable at one end to a crane-type workpiece, and securable at a second end to a force measurement apparatus.

19. The force application and measurement apparatus of claim 2, where the vertical posts include a plurality of sockets along their length, and wherein the sockets are adapted to receive the upper component at a plurality of different heights.

\* \* \* \* \*